United States Patent [19]

Dulebohn

[11] Patent Number: 5,201,741
[45] Date of Patent: Apr. 13, 1993

[54] SURGICAL SNARE WITH SHAPE MEMORY EFFECT WIRE

[75] Inventor: David H. Dulebohn, Tonka Bay, Minn.

[73] Assignee: Andrew Surgical, Inc., Plymouth, Minn.

[21] Appl. No.: 557,536

[22] Filed: Jul. 24, 1990

[51] Int. Cl.⁵ .......................................... A61B 17/00
[52] U.S. Cl. .................................. 606/113; 606/45; 606/110
[58] Field of Search ........................... 606/110–114, 606/127, 78, 39, 45, 46; 128/4–11

[56] References Cited

U.S. PATENT DOCUMENTS

| | | | |
|---|---|---|---|
| 3,828,790 | 8/1974 | Curtiss et al. | 128/320 |
| 3,955,578 | 5/1976 | Chamness et al. | 128/303.15 |
| 4,256,113 | 3/1981 | Chamness | 128/303.14 |
| 4,294,254 | 10/1981 | Chamness | 128/303.14 |
| 4,326,530 | 4/1982 | Fleury, Jr. | 128/303.14 |
| 4,345,599 | 8/1982 | McCarrell | 128/320 |
| 4,493,320 | 1/1985 | Treat | 128/303.15 |
| 4,665,906 | 5/1987 | Jervis | 606/78 |
| 4,718,419 | 1/1988 | Okada | 128/303.15 |
| 4,732,150 | 3/1988 | Keener, Jr. | 128/320 |
| 4,926,860 | 5/1990 | Stice et al. | 606/144 |
| 4,991,602 | 2/1991 | Amplatz et al. | 604/164 |

FOREIGN PATENT DOCUMENTS

| | | | |
|---|---|---|---|
| 0023914 | 4/1906 | Fed. Rep. of Germany | 606/113 |
| 0140158 | 4/1960 | U.S.S.R. | 606/113 |

OTHER PUBLICATIONS

"Nitinol—Metal with a Memory", 2 page document.
Special Metals Corp., New Hartford, N.Y. 13413, 2 page document.
I. Introduction, Nitinol is a Shape Memory Effect . . . , 19 page document.

Primary Examiner—Stephan C. Pellegrino
Assistant Examiner—Glenn K. Dawson
Attorney, Agent, or Firm—Zarley, McKee, Thomte et al.

[57] ABSTRACT

A surgical snare having a wire which forms the snare loop made from a shape memory effect metallic alloy which exhibits superelasticity at room temperature. The wire is trained so that it assumes an intermediate snare loop size in an unrestrained free state. From this trained free state configuration, the loop can be expanded to a large loop and contracted to a very small loop without permanent deformation from the trained intermediate state. This range of movement enables an expanded range of applicability for snares in general, and also enables reducing the instrument tip size with improved loop configuration.

12 Claims, 6 Drawing Sheets

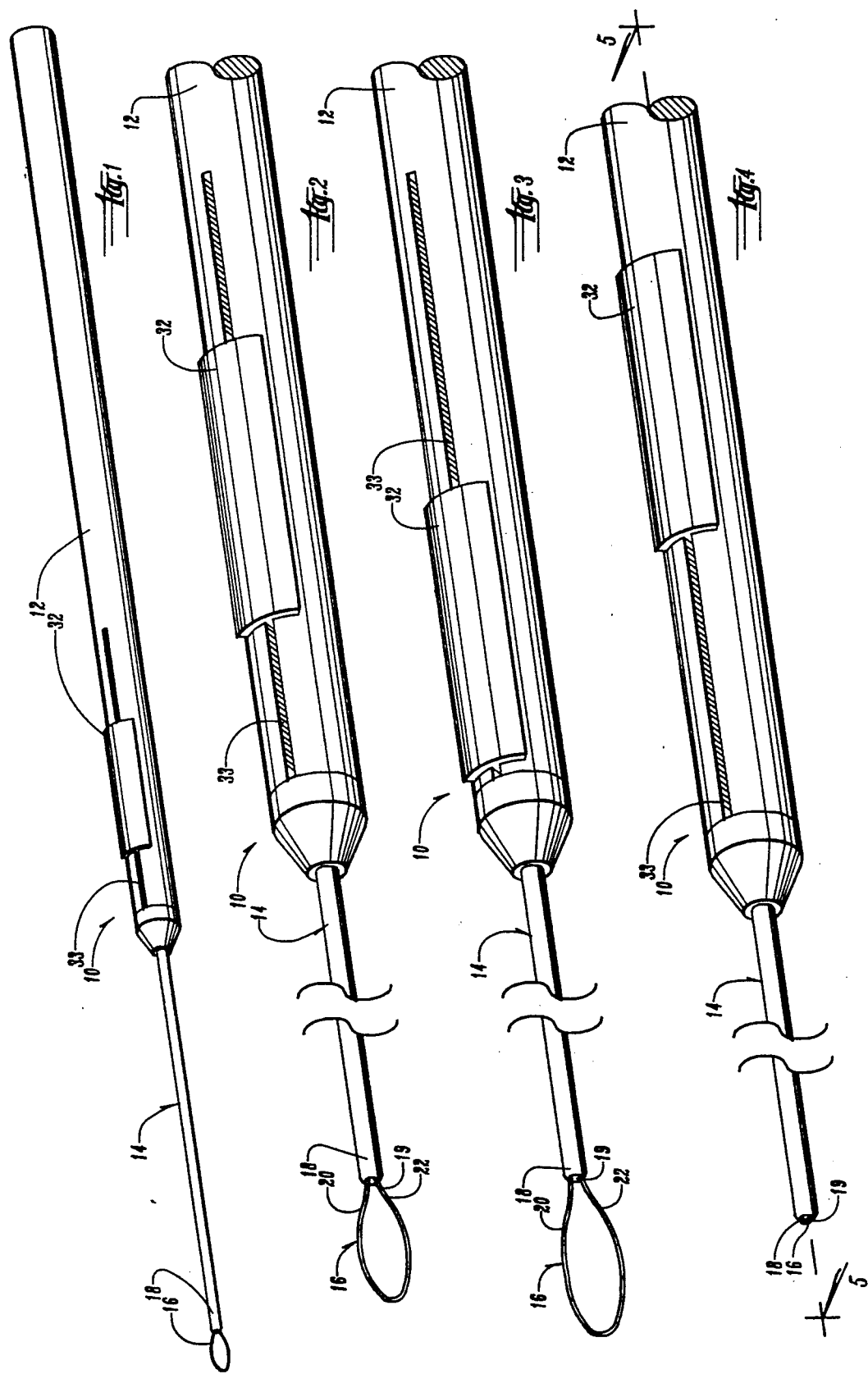

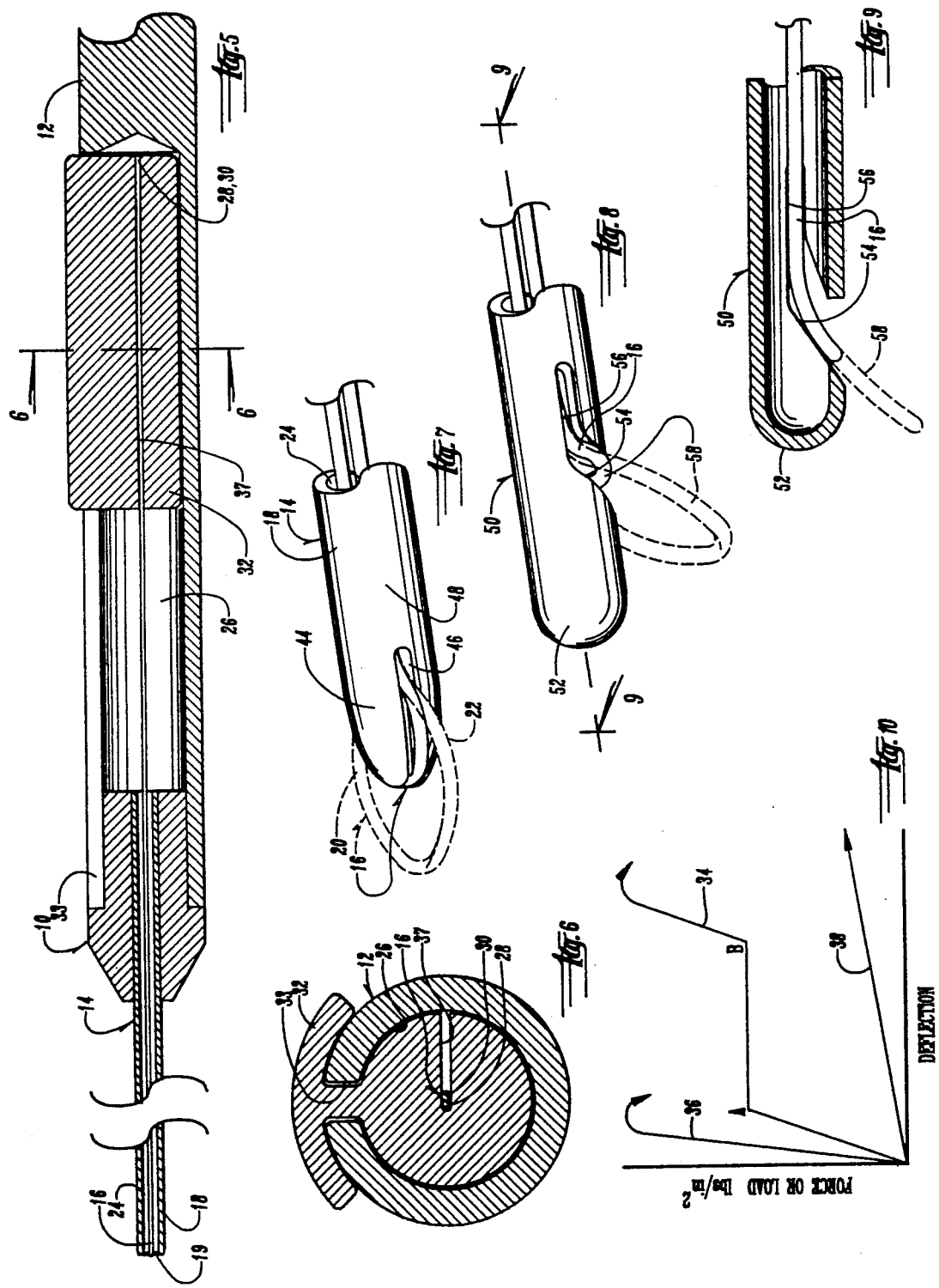

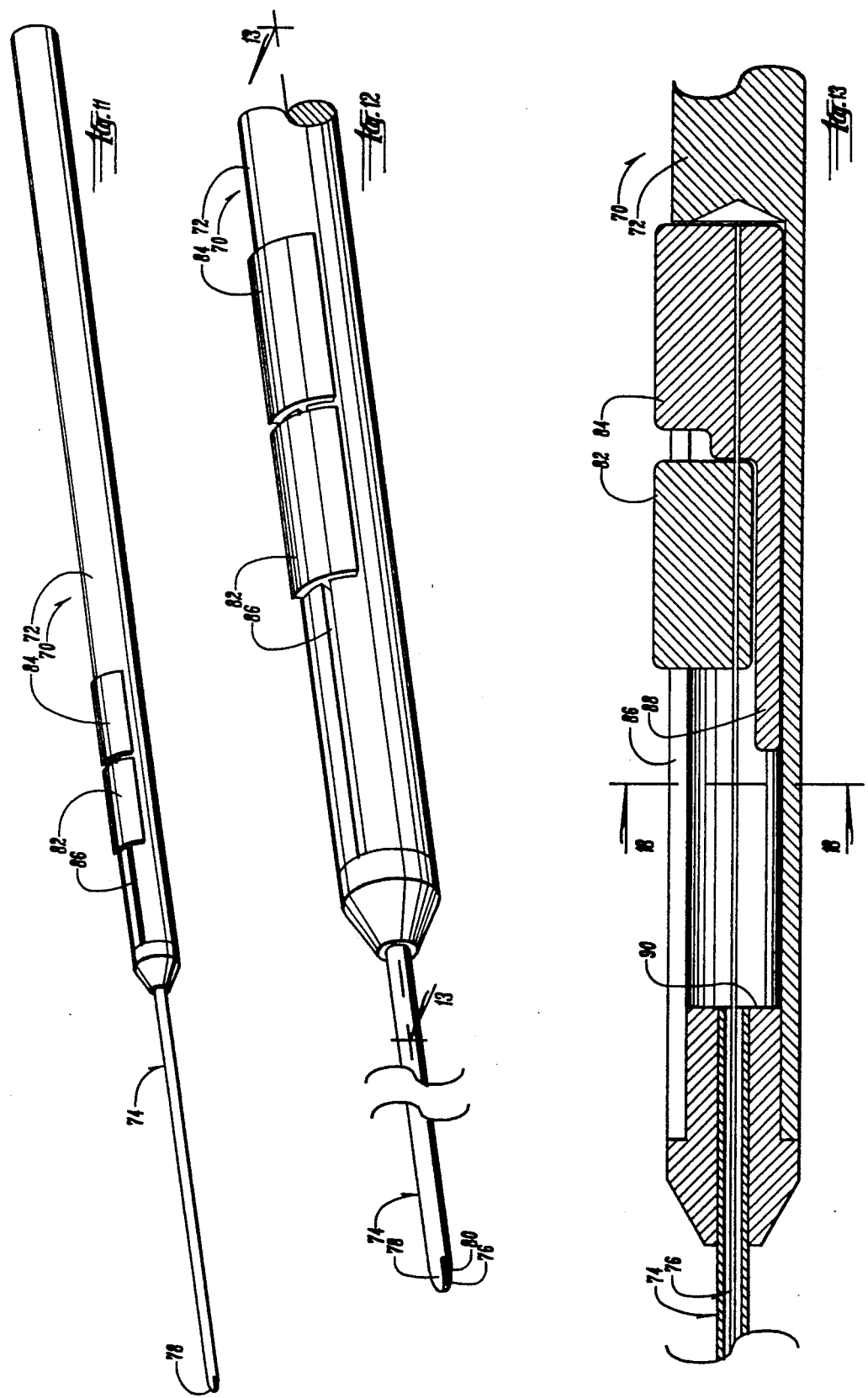

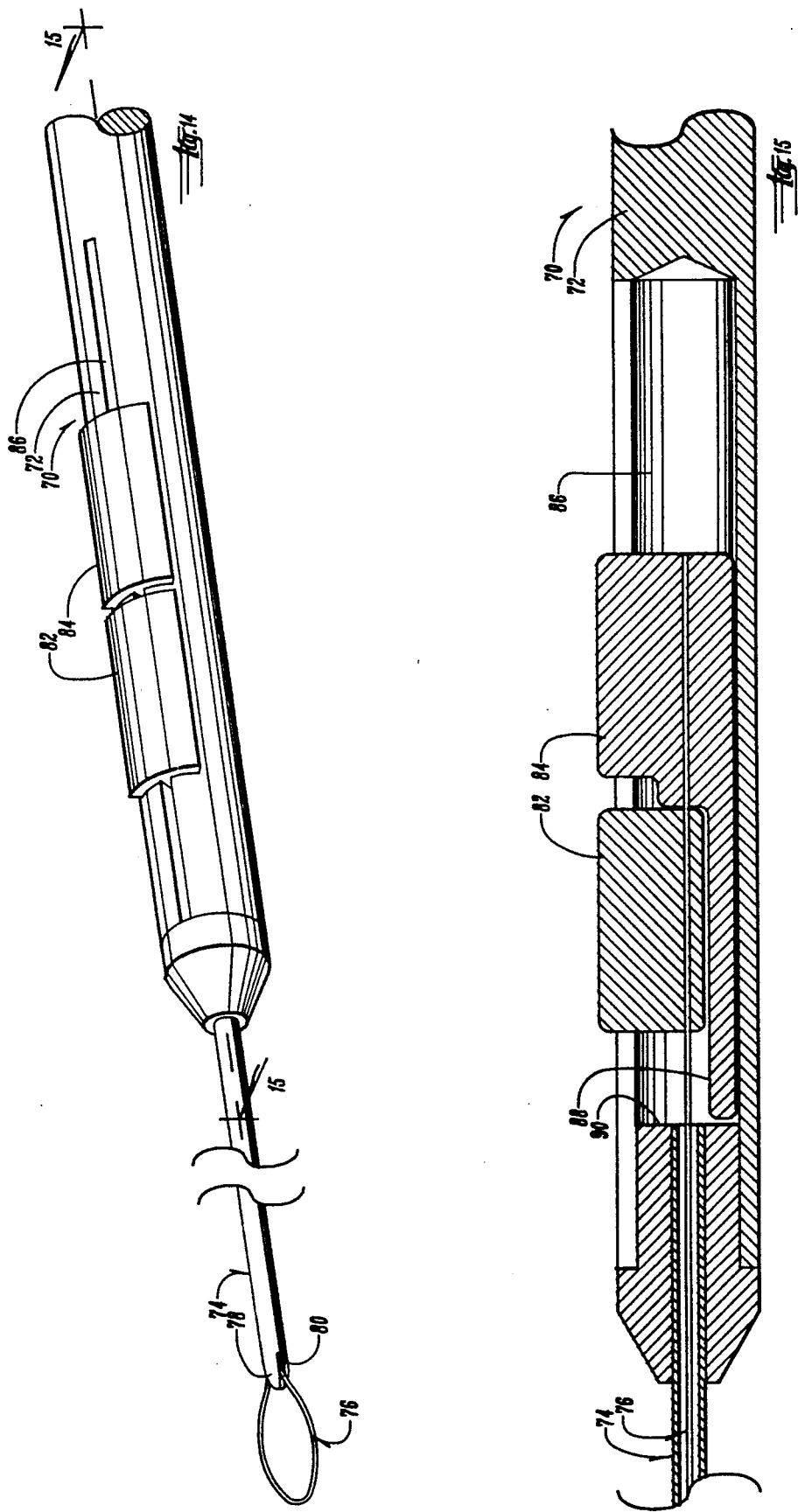

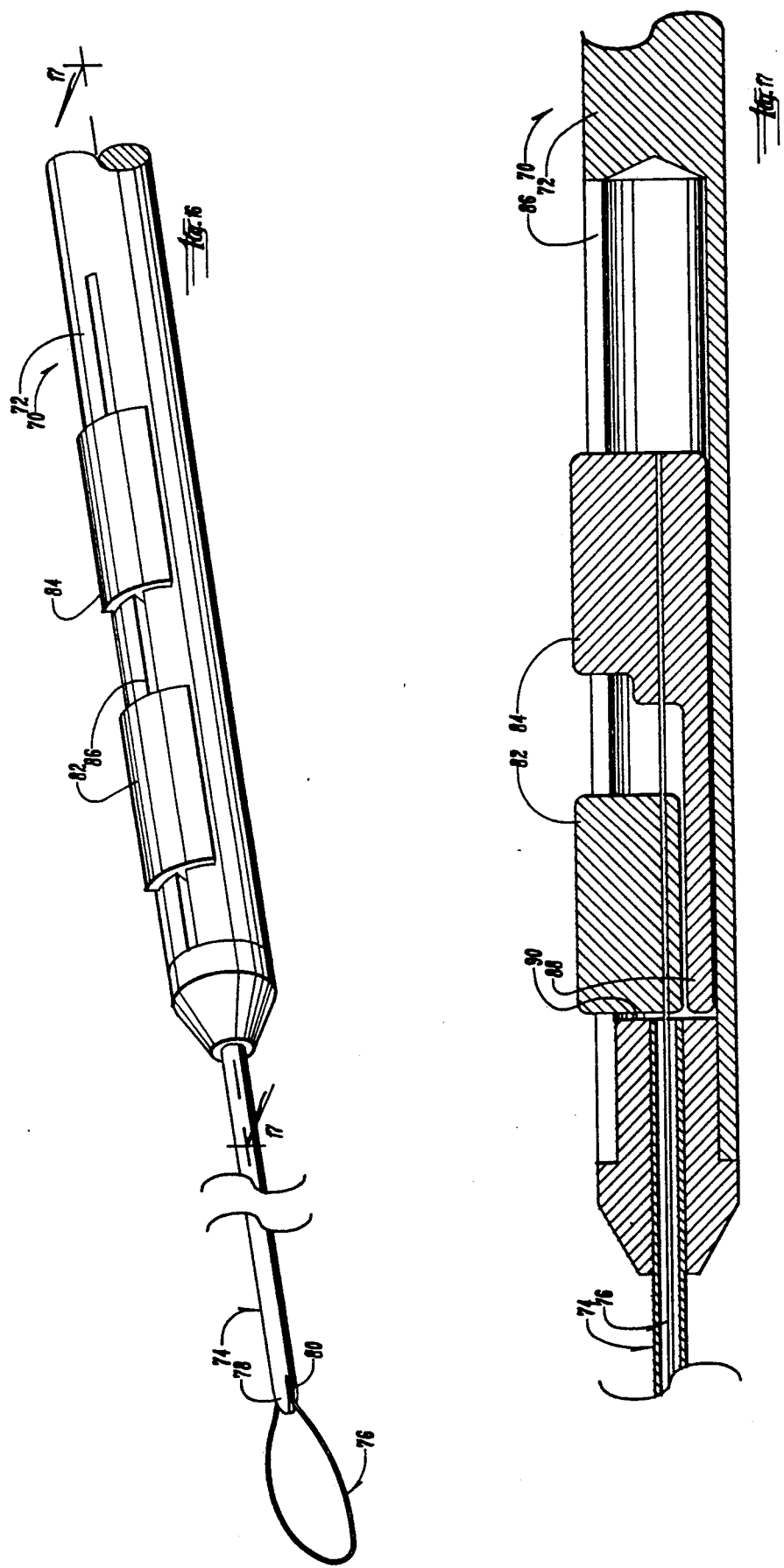

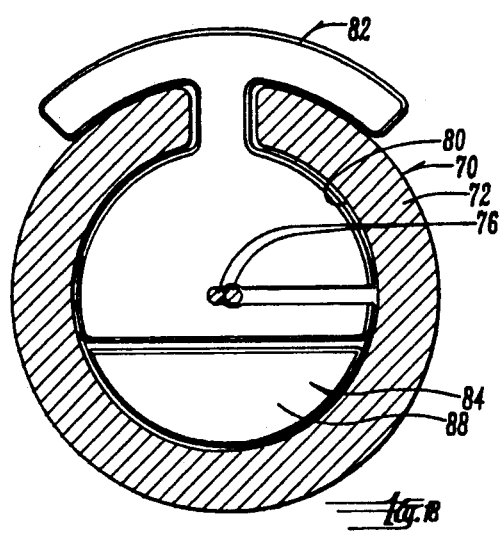
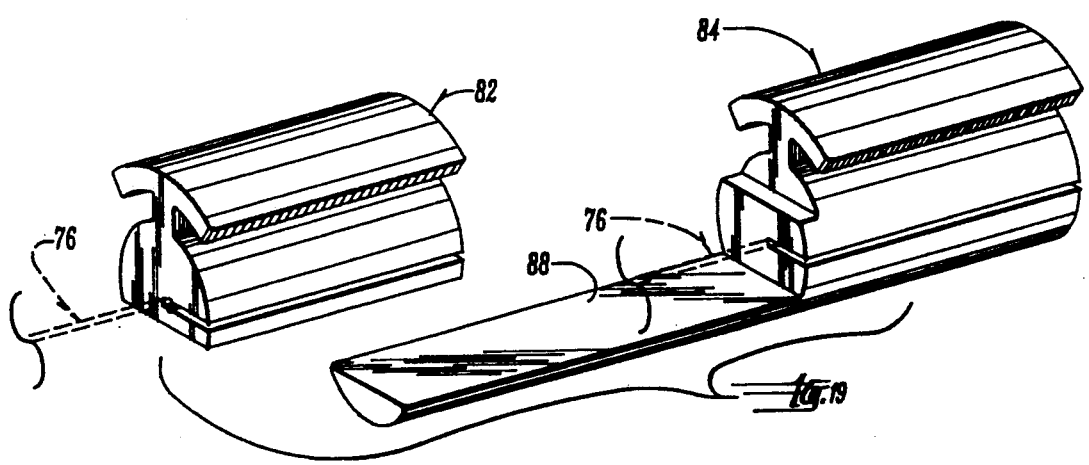

SURGICAL SNARE WITH SHAPE MEMORY EFFECT WIRE

BACKGROUND OF THE INVENTION

A. Field of the Invention

The present invention relates to medical surgical instruments, and in particular to surgical snare-type instruments for cutting or retrieving.

B. Problems in the Art

Surgical snares are well known within the medical field. A small loop is formed at the end of a narrow tip of the instrument. The tip is inserted through an incision or orifice and moved to a location which requires cutting of tissue or retrieval of matter. To cut, the targeted material is surrounded by manipulating the instrument to correctly position the loop. The loop is pulled into the tip to sever the surrounded tissue. Alternatively, the loop can be positioned to surround and then retrieve the desired matter.

The value of a surgical snare is that it can be inserted into a relatively small incision or orifice and it can reach into areas difficult to access. By utilizing known methods, the surgeon can locate the targeted material to be cut or retrieved and then the instrument can be withdrawn from the same small incision or opening. This greatly minimizes the trauma to the patient. The larger the incision or intrusion of surgical instruments to the body, the more trauma and damage. This requires substantial repair and suturing, which in turn requires a greater recovery time and more care during that time.

The uses of surgical snares are also well known. Examples are the removal of polyps and tonsils, and prostate surgery. Other applications are possible. Snares can be used whenever bits of tissue need to be severed, or pieces of material must be retrieved with minimum trauma caused by insertion of the instrument to that location.

Examples of different types of surgical snares can be found in the following issued United States patents:

| U.S. Pat. No. | Inventor | Issue Date |
| --- | --- | --- |
| 3,828,790 | Curtiss, et al. | August 13, 1974 |
| 3,955,578 | Chamness, et al. | May 11, 1976 |
| 4,256,113 | Chamness | March 17, 1981 |
| 4,294,254 | Chamness | October 13, 1981 |
| 4,326,530 | Fleury, Jr. | April 27, 1982 |
| 4,345,599 | McCarrel | August 24, 1982 |
| 4,493,320 | Treat | January 15, 1985 |
| 4,718,419 | Okada | January 12, 1988 |
| 4,732,150 | Keener, Jr. | March 22, 1988 |

As can be seen, most of these snares utilize a loop of wire as a snare, where the lop is formed by adjacent ends of two pieces of wire being welded or otherwise secured together. The only exceptions to this are the McCarrel reference which uses a single strand of wire connected to a movable rod at the instrument tip end, and Keener, Jr. which also uses a single strand.

In the above described patents, stainless steel wire is used to form the loops. In single strand loops, unless the wire diameter is extremely small, the loop cannot be contracted to a very small size without permanent deformation of the wire.

In the fully contracted state, a very small loop is mandatory to allow the loop to be completely withdrawn into the tip. Complete withdrawal is necessary to perform the function of cutting tissue.

Consequently, in single strand snare loops made of conventional stainless steel wire, the tip must be made large to accommodate a large loop, or the wire diameter must be reduced considerably to enable contraction of the loop within the tip within the elastic limit of the stainless steel. This trade-off places severe limits on the design of conventional single wire snares. The larger tube is undesirable, and the thinner wire is so fragile that its use is extremely limited.

The dual wire snare was developed to overcome the above described limitations. Two parallel wires are welded together at one end and then formed to produce a loop. This design enables full contraction of the wires into a very small tip, however, the resulting oblong loop configuration is not good, and the surgeon must contend with the sharp tip at the juncture of the wires.

It is therefore a principle object of the present invention to provide a surgical snare with shape memory effect wire which overcomes or solves the problems and deficiencies in the art.

Another object of the present invention is to provide a snare loop which expands into a more rounded or circular configuration.

Another object of the present invention is to provide a surgical snare as above described which can be contracted to a very small loop, or expanded to a larger loop without permanent deformation.

A still further object of the present invention is to provide a surgical snare as above described which allows the snare loop to be made from one piece of wire.

Another object of the present invention is to provide a surgical snare as above described which allows the contracted loop to be only slightly larger in outside diameter than the outside diameter of the instrument tip end to facilitate insertion through smaller incisions or openings.

A still further object of the present invention is to provide a single wire surgical snare as above described which allows the diameter of the surgical instrument tip to be made smaller than conventional surgical snares so that the entire apparatus can be inserted through incisions and openings smaller than conventional surgical snares.

Another object of the present invention is to provide a surgical snare as above described which is durable, compatible with surgical procedures, non-corrosive, safe, and efficient.

These and other objects, features, and advantages of the present invention will become more apparent with reference to the accompanying specification and claims.

SUMMARY OF THE INVENTION

The invention allows surgical snares to have the wire snare loop made of one piece of wire, while at the same time allowing greater degrees of expansion and contraction of the one piece loop than previously possible. The wire is a shape memory effect material that can be trained to assume a specific loop shape. The trained loop shape is wider than the diameter of the tubular tip of the instrument. The ends of the wire pass through the tubular tip into a handle, to which the tip is attached. Normally, a control means is attached to the wire ends so that the ends either concurrently or individually can be moved to alter the shape of the loop outside the tip end.

Alteration of the shape of the loop can be either to expand its shape past its normal loop configuration, or to contract its shape smaller than its normal loop configuration. The expansion is generally to allow the surgeon to envelope or surround tissue or matter to be cut or retrieved. The retraction to the contracted state is to either insert the instrument tip through a small surgical incision or other opening, or to perform the cutting operation. It can also be retracted to grasp and hold matter to be retrieved and retracted out of the surgical incision or other opening.

Shape memory alloys are generally referred to as metals with a memory, and they are also generally superelastic. It is this latter feature that is utilized in the present invention. Specific shape memory alloys are approximately four times more flexible than conventional stainless steel. Repeated expansions and contractions over a large change in loop size can be made without permanent deformation.

The invention therefore allows the loop to be made from one piece of material, eliminating the need for attachment of two pieces together. It also allows the loop to be contracted into a small diameter tip so that the instrument can both cut and be inserted into very small incisions or other openings. This is a valuable advantage because it minimizes the trauma to a patient.

BRIEF DESCRIPTION OF THE DRAWINGS

FIG. 1 is a perspective view of the invention showing the general configuration of one embodiment of the invention.

FIG. 2 is an enlarged partial perspective view of the tip end of the device of FIG. 1 showing the snare loop in an intermediate position.

FIG. 3 is a perspective view similar to FIG. 2 but showing the snare loop in its "trained state" which corresponds with its fully expanded position.

FIG. 4 is a perspective view similar to FIGS. 2 and 3 but showing the snare loop in a contracted or closed position.

FIG. 5 is a sectional view taken along line 5—5 of FIG. 4.

FIG. 6 is a sectional view taken along line 6—6 of FIG. 5.

FIG. 7 is an enlarged partial cutaway, partial perspective view of an alternative embodiment of a tip end which could be used with the invention.

FIG. 8 is an enlarged partial cutaway and a perspective view of a still further optional embodiment of a tip end.

FIG. 9 is a sectional view taken along line 9—9 of FIG. 8.

FIG. 10 is a graph showing the general elasticity characteristic of shape memory effect material, compared to stainless steel and plastic.

FIG. 11 is a perspective view of an alternative embodiment for the invention.

FIG. 12 is an enlarged partial perspective view of the tip end and control mechanism for the alternative embodiment of FIG. 11. FIG. 12 shows the snare loop in a fully retracted position.

FIG. 13 is a sectional view taken along line 13—13 of FIG. 12.

FIG. 14 is a similar view to FIG. 12 but showing the control mechanism operated to enlarge the snare loop to its trained position.

FIG. 15 is a sectional view taken along line 15—15 of FIG. 14.

FIG. 16 is a similar view to FIGS. 12 and 14 but showing the control element operated to enlarge the snare loop to a greater extent than the trained position of FIG. 14.

FIG. 17 is a sectional view taken along line 17—17 of FIG. 16.

FIG. 18 is a sectional view taken along line 18—18 of FIG. 13.

FIG. 19 is an exploded perspective view of the control elements of the embodiment shown in FIGS. 11-18.

DETAILED DESCRIPTION OF THE PREFERRED EMBODIMENT

In order to assist in an understanding of the invention, a description of preferred embodiments of the invention will now be made in detail. It is to be understood that this description is not intended, nor does it necessarily limit the invention.

The attached drawings will be referred to in this description. Reference numerals will be used to indicate selected parts and locations in the drawings. The same reference numerals will be used in all the drawings for the same parts or locations, unless otherwise indicated.

FIG. 1 illustrates in perspective one preferred embodiment according to the present invention. The surgical snare 10 includes a handle portion 12, a tip portion 14, and a wire loop or snare 16. As can be seen in FIGS. 5 and 6, wire loop 16 is extendable from distal end 18 of tip 14. It is made from one piece of wire and has side-by-side intermediate sections 20 and 22 which extend through hollow bore 24 of tip 14 back into the interior 26 of handle 12.

Free ends 28 and 30 of wire loop 16 are respectively attached to a control member 32 which is slidable along handle 12. As can be appreciated, sliding of control member 32 to the left or right in FIG. 1 will cause expansion and contraction respectively of wire loop 16. The surgeon can therefore control loop 16 at handle 12 in this way. In FIG. 1, the wire loop is in a partially extended, partially expanded intermediate loop configuration.

Wire loop 16 is made from a shape memory effect material (abbreviated SME material). A wire made of this material can be trained to remember a specific free state configuration, and because this material is superelastic, it can be severely deformed from the trained configuration and still return to the trained configuration.

The material is trained by heating it to a specific temperature while restraining it in the desired configuration.

SME metal alloys owe their superelastic properties to a phenomenon called stress induced room temperature martensitic phase transformation. This is illustrated in FIG. 10 which also compares SME materials with stainless steel and plastic materials such as nylon.

In FIG. 10, the abscissa depicts deflection or bending of a wire whereas the ordinate depicts the load or bending force upon the wire. FIG. 10 is basically a series of stress-strain curves for the various materials.

Line 36 in FIG. 10 illustrates that stainless steel deflects only a small amount before reaching the elastic limit where the relation of stress to strain becomes non-linear.

Line 38 in FIG. 10 illustrates that plastic materials such as nylon deflect considerably more than metals. The yield point where the elastic limit is reached is off the chart.

Line 34 in FIG. 10 illustrates that SME alloys maintain a linear stress-strain relation up to point "A" where a stress plateau starts. At this point, the SME metal starts going through a stress induced phase transformation that continues to point "B" with little stress being added. The transformation is complete at point "B", and the normal linear stress-strain relation resumes up to the yield point. This illustration shows that the SME material bends approximately four times more than stainless steel within the elastic limit of the material.

The effects and theories surrounding SME materials are well documented. Following is a short list of references which are incorporated by reference:

International Conference on Martensitic Transformations, Aug. 26–30, 1986, NARA, Japan, Japan Institute of Metals.

International Symposium on Shape Memory Alloys, Sep. 6–9, 1986, Guilin, China Academic Publishers.

Shape Memory Effect in Alloys, Jeff Perkins, Editor, Plenum Press, 1975.

Andreasen, George, Shape Memory Alloys, *Encyclopedia of Medical Devices and Instrumentation* J. Wiley & Sons, 1987.

Schetky L. McDonald, Shape Memory Alloys, "Scientific American", Nov. 1979, pgs. 74–82.

Wayman, C. Marvin, Some Applications of Shape Memory Alloys, "Journal of Metal", Jan. 1980, pgs. 129–137.

55-Nitinol-The Alloy With A Memory, Its Physical Metallurgy, Properties and Applications, C. M. Jackson, Editor, NTIS, N72-30468, 1972.

Shape Memory Alloys, 1975–Nov. 1985, Citations From INSPEC, NTIS, PB86-85079/XAB.

Shape Memory Alloys, 1970–Nov. 1975, Citations From Engineering Index Data Base, NTIS, PB86-851888/XAB.

Nitinol Development and Applications. 1977-Jan. 1984, Citations From Energy Data Base NTIS PB84-859149.

A Source Manual For Information on Nitinol and NiTi, David Goldstein, Editor, Feb. 1980, Naval Surface Weapons Center.

D. Goldstein, et al., "Stress Effects on Nitinol Phase Transformations", *Journal of Metals.* Vol. 39, Mar. 1987, pgs. 19–26.

The particular properties of SME materials will therefore not further be discussed except as relevant to the present invention.

In the preferred embodiment, wire loop 16 is made from Nitinol, an SME metal alloy composed of approximately 50% each of nickel and titanium. Nitinol is available from a variety of vendors including Shape Memory Applications, Inc., 285 Sobrante Way, Suite E, Sunnyvale, Calif. 94086 or Special Metals Corporation, Middle Settlement Road, New Hartford, N.Y. 13413.

FIG. 2 is an enlarged view of tip end and control portions of snare 10 as shown in FIG. 1. Control member 32 is in an intermediate position along slot 33 in handle 12. This illustrates how member 32 can be slid along slot 33. Snare loop 16 is likewise in an intermedite expanded and extended position. It is neither in its "trained state" nor is it fully contracted into tip end 18.

By referring to FIG. 3, it can be seen that by operating control member 32 (by moving it towards tip 14), wire loop 16 can be moved to its fully expanded trained state. The SME material of loop 16, in its "trained" configuration in FIG. 3, forms a nice, smooth loop.

Once inserted through an incision or opening (during insertion the loop 16 is generally moved to its contracted position on FIG. 4) the loop can be expanded from its contracted position of FIG. 4, through intermedite positions exemplified by FIG. 2, to its fully expanded, trained state shown in FIG. 3, and the distal end 18 of tip 14 can be manipulated to place the expanded loop around material or tissue to be cut or surround the material to be cut or retrieved. The high elasticity allows the expansion and contraction of loop 16 between contracted and "trained" configurations of FIGS. 4 and 3 without permanent deformation.

FIG. 4, essentially similar to FIGS. 2 and 3, then shows the elasticity of wire loop 16 as it is brought into its most contracted state. Control member 32 is simply moved in the opposite direction pulling ends 28 and 30 to the point where wire loop 16 is almost completely enveloped into distal end 18 of tip 14 of surgical snare 10. As can be seen, the wire loop 16 is extremely small compared to the "trained" loop of FIG. 3. In addition, the ratio of the diameter of the wire to inside diameter of tip for the type of surgical snares disclosed herein could be as close as approximately 1:5. Again, the high elasticity of the SME material allows it to take on the configuration of FIG. 4 without permanent deformation. Upon return of control member 32 to the position shown in FIG. 3, wire loop 16 will return to its "trained" form shown in FIG. 3. This can be repeated without permanent deformation.

The nature of SME material is that it retains it elasticity and therefore has good effective life for a surgical instrument of this type. The advantages of rigidity of the metal alloy allows it to cut as effectively as other metal wire, and it is also highly corrosion resistant, more so than conventional metals, even stainless steel. Furthermore, its inherent biocompatible nature makes it an attractive selection for surgical use.

As applied to the preferred embodiment, the material for wire loop 16 is selected and trained so that the loop of FIG. 3 is satisfactory in size and shape so that movement between the contracted or trained states of FIGS. 4 and 3 stays within the elastic limit of the material, as indicated in the graph of FIG. 10. No risk of deformation or breakage then exists.

FIGS. 5 and 6, as previously referred to, show in sectional views the exact configuration of the interior of instrument 10. In particular, FIG. 5 shows how the SME wire 16 extends through the interior of tip 14 and interior of handle 12 to its connection to control member 32. Wire 16 is placed into a slot 37 that extends the length of member 32, but extends only approximately half way transversely into member 32. It can also be seen how control member 32 can slide within handle 12 along slot 33.

Likewise, FIG. 6 shows in detail how both ends 28 and 30 of wire 16 are inserted into slot 37 or control member 32, and how this special shape of control member 32 allows it to slide as well as be retained within handle 12 by having a portion extend through slot 33 to the exterior of handle 12 for manual slideable adjustment along handle 12. It is to be understood that ends 28 and 30 of wire 16 can be secured in slot 37 of control member 32 by a number of different methods such as are well within the skill of those of ordinary skill in the art. One way would be to weld the wire ends in place. Another would be to secure end caps (not shown) to ends 28 and 30, which would prevent longitudinal movement of wire 16 within slot 37 of member 32. The ends could also be fixed by some type of adhesive. Other ways are possible.

It is to be noted that the embodiment of snare 10 shown in FIGS. 1 through 6 utilizes a distal tip end 18 which has a smooth and rounded outer surface to the extent possible, while retaining the opening for the loop 16 to be drawn into tip 14. This is to reduce, as much as possible, edges or surfaces which would tend to catch or otherwise cause trauma during insertion of tip 14.

FIG. 7 is an isolated enlarged view of an alternative tip end 44 for use with the present invention. It is formed with a hemispherical end and a slot 46 exists transversely across and longitudinally inwardly along distal end 48. As can be seen, this allows wire loop 16 to be contracted into distal end 48 and to substantially seal the end without permanent deformation of the wire. The slot provides cutting edges for severing tissue that is enveloped within the loop. It is to be understood that the curved outside radius of wire loop 16 actually enhances the ease by which snare 10 can be inserted into a small incision or opening because of its rounded surfaces. Loop 16 is shown in a somewhat extended position in dashed lines.

As can be seen in FIG. 7, slot 46 allows loop 16 to be retracted into tip 14 in such a fashion that even though the distal end is narrow and rounded to its hemispherical shape, the loop can be pulled virtually entirely into the tip, except for opposite sides which slightly extend out of opposite sides of slot 46. This again enhances the ability for the snare to contract down to a very small diameter loop, pull tissue into the tip end, and cut the tissue without exceeding its limits of elasticity and permanently deforming. The rounded surfaces of the SME wire comprising loop 16 minimizes the edges which could cause catching of tissue or otherwise cause trauma to tissue during insertion or retraction of tip 14.

FIG. 8 shows a still further isolated enlarged embodiment for an alternative tip end 50 according to the invention. Tip end 50 has a closed rounded or hemispherical end 52 comprising its extreme distal end 52. An angled slot 54 is located proximally to distal end 52 and forms the opening out of which wire loop 16 is extendable. A slot 56 also exists along the longitudinal axis of tip 50 behind angled slot 54.

The arrangement of FIG. 8 is a means for the surgical snare to retrieve matter from the patient as opposed to cutting tissue. The wire loop 16 is extendable out at an angle from the longitudinal axis of the snare once inserted into the patient and expanded. The instrument can then be manipulated, wire loop 16 enlarged and surrounded around the targeted matter, and the matter to be retrieved then can be cinched to the tip by contracting wire loop 16 with a control member such as described above. The retrieved piece and the instrument can then be retracted from the incision or opening. Loop 16 is shown in solid lines in a retracted state in FIG. 8. It is to be understood that wire loop 16 can be "trained" to normally take the configuration shown at dashed lines 58. Contractions into tip end 50 to the contracted configuration and expansions to trained state 58 will then again be within the elastic limits for the SME material.

It will be appreciated that the present invention can take many forms and embodiments. The true essence and spirit of this invention are defined in the appended claims, and it is not intended that the embodiment of the invention presented herein should limit the scope thereof. As can be appreciated, different tip shapes can be utilized. Various types of SME materials can be used for the wire loop and different shapes of both tip and handle can be used.

Still further, different types of control mechanisms can be used. For example, a differential motion control can be used whereby each end of the wire loop is attached to an independently slidable control member. The loop shape can then be manipulated in more ways by moving the control elements either singly or in different combinations to one another.

An example of this type of differential motion control can be seen at FIGS. 11-19. FIG. 11 shows surgical snare 70 having a handle 72, tip 74, and SME alloy wire loop 76. Distal end 78 of tip 74 is configured like that shown in FIG. 7, including a slot 80. It is to be understood, however, that other end types could be used such as shown in FIG. 1 or FIG. 8. The operation and structure of snare 70 is essentially the same as that of snare 10 shown and described with respect to FIGS. 1-9 except for the following. Instead of one control element 32, first and second control elements 82 and 84 are associated with handle 72, as can be seen in FIG. 11. Both elements 82 and 84 are slideable along slot 86 in handle 72. The advantage of the differential motion allowed by first and second control elements 82 and 84 is depicted in FIGS. 12-17.

By comparing FIGS. 12, 14, and 16, it can be seen that snare loop 76 can be adjusted from its retracted and closed position (FIG. 12), to an intermediate trained position (FIG. 14), and then to a still further expanded position (FIG. 16). It is to be understood, by referring to FIGS. 13, 15, 17, 18, and 19, that one end of SME wire 76 is secured to control element 82; whereas the other end of wire 76 is connected control element 84. The control elements 82 and 84 can therefore be moved to a certain extent in unison, or to a certain extent individually. This allows a significant amount of enhanced ability to adjust the loop size and shape, which can be advantageous to certain procedures.

FIGS. 12 and 13, showing loop 76 in its contracted state, also show control elements 82 and 84 moved in abutment to one another to position farthest away from tip 74 of snare 70. The proximal end of slot 86 serves as an end stop for control elements 82 and 84 which in turn defines how far into tip 74 loop 76 can be moved.

FIGS. 14 and 15 show how control elements 82 and 84 can be moved to an intermediate position along slot 86, but still in abutment to one another, to produce the expanded loop shown in FIG. 14. In this embodiment, loop 76 is at its "trained" position. As can be seen in FIG. 15, the extended portion of 88 control element 84 comes into abutment with an interior wall 90 of ferrule 72, when in the position shown in FIGS. 14 and 15, limiting any further movement of control element 84 towards tip 74.

However, this does allow control member 82, which is not so limited, to be moved further towards tip 74, as is shown in FIGS. 16 and 17. This allows one side of the wire 76 to be pushed further out of tip 14 to expand the loop to its maximum expanded form shown in FIG. 16. This is beyond the "trained state" of loop 76, but not beyond its limit of elasticity. Interior wall 90 serves as an end stop for control element 82 to limit expansion of loop 76.

It is to be understood, however, that control element 82 can at any time and in any relation to control element 84 be separately moved to vary the shape of loop 16 according to desire.

FIGS. 18 and 19 show with more specificity the relationship of control members 82 and 84 to one another and to the connection to the ends of SME wire loop 16.

It can therefore be seen that the differential movement advantageously allows more flexibility in the manipulation of the loop size to take advantage of the superelasticity, without permanent deformation of the SME loop, such as has been previously described.

Other methods of control of the loop, control member and and shape of configuration, method of attachment of the SME loop ends to the control element, handle shapes, tip shapes and configurations, and dimensions are possible.

What is claimed is:

1. A surgical snare device comprising:
    a handle means for holding and controlling the snare;
    a tip means having a distal end extending from the handle means and having a hollow channel therethrough;
    a wire means having first and second ends positioned in the handle means, the remainder of the wire means extending through the handle means and hollow channel of the tip means to a loop end, the wire means comprising a shape memory effect material; a control means associated with the handle means for moving the first and second ends of the wire means within the handle means to move the loop from a position substantially enveloped by the distal end of the tip means to positions outside the tip means and to alter the size of the loop end of the wire means when outside the tip means; the loop end being alterable in shape by movement of the control means and adjustable between a plurality of expanded positions and a contracted position where the loop end is retracted into the distal end of the tip means, the shape memory material being trained to form a loop end wider than the distal end of the tip means but allowing contraction of the loop end substantially into the distal end of the tip means without permanent deformation of the wire means, and to allow expansion of the loop end beyond the trained size to the expanded positions without permanent deformation of the wire means;
    the tip means including a hemispherical distal end including a slot transversely through opposite sides of the distal end to receive at least a portion of the loop end when in a retracted position.

2. The device of claim 1 wherein the ratio of the diameter of the wire means to the inside diameter of the distal end of the tip means is approximately 1:5 or greater.

3. The device of claim 1 wherein the shape memory material is a shape memory alloy.

4. The device of claim 3 wherein the shape memory alloy is a nearly equiatomic alloy of nickel and titanium.

5. The device of claim 1 wherein the control means comprises a slide element slidably connected to the handle means.

6. The device of claim 1 wherein the control means has independent controls for each of the first and second ends of the wire means to allow for differential motion between said ends.

7. A surgical snare instrument including a handle, a tip with hemispherical distal end extending from the handle, a wire loop extending from the tip having first and second ends positioned in the handle with intermediate portions extending through at least a portion of the handle to the tip, and control means attached to the first and second ends of the wire moveable with respect to the handle to in turn contract or expand the loop, the improvement comprising:
    the wire loop being comprised of shape memory material trained to a loop shape;
    the wire loop being adjustable between a fully expanded and a fully contracted loop end size, the wire loop being trained to a loop end size intermediate between the fully expanded and fully contracted loop end sizes so that said wire loop can be contracted to a size equal to or only slightly larger than the inside diameter of the tip to allow the inside diameter of the tip to be as small as possible for passage of the tip and wire loop through as small an opening as possible, and allowing expansion of the loop end beyond said intermediate size to assist in surrounding a targeted item, the fully expanded and fully contracted loop end sizes not exceeding the limits of elasticity of the shape memory effect material.

8. The instrument of claim 7 wherein the ratio of the diameter of the wire of said wire loops to the inside diameter of the tip is approximately 1:5 or greater.

9. A method of maximizing a wire diameter while minimizing the diameter of a snare tip, for the wire of a surgical snare instrument, comprising:
    forming a loop end of the wire of the surgical snare at least in part of shape memory effect material;
    training the loop end to an intermediate size between a fully contracted loop end size having a diameter equal to or only slightly larger than an inside diameter of the snare tip of said surgical snare instrument and an expanded shape larger than the intermediate shape, where the expanded shape and fully contracted shape do not exceed the limits of elasticity of the shape memory effect material;
    enabling the wire of the surgical snare to be deformed into the loop end which can be reduced to a very small size for insertion into the tip and return to an increased size out of the tip without permanent deformation of the wire of the surgical snare, thus enabling the diameter of the wire to be maximized while minimizing the inside diameter of the tip of the instrument.

10. The method of claim 9 wherein the diameter of the wire is selected to be approximately one-fifth the size or smaller of the inside diameter of the tip of the surgical snare.

11. The method of claim 9 wherein the wire is selected from a shape memory effect alloy.

12. The method of claim 11 wherein the shape memory effect alloy is Nitinol.

* * * * *